United States Patent
Rehder et al.

(10) Patent No.: US 8,669,111 B2
(45) Date of Patent: Mar. 11, 2014

(54) BUFFERS FOR STABILIZING BIOLOGICAL SPECIMENS AND THEIR USE

(71) Applicant: Arizona Board of Regents, a body corporate acting for and on behalf of Arizona State University, Scottsdale, AZ (US)

(72) Inventors: Douglas Rehder, Phoenix, AZ (US); Matthew Schaab, Phoenix, AZ (US); Chad Borges, Avondale, AZ (US)

(73) Assignee: Arizona Board of Regents, A Body Corporate of the State of Arizona Acting for and on Behalf of Arizona State University, Scottsdale, AZ (US)

(*) Notice: Subject to any disclaimer, the term of this patent is extended or adjusted under 35 U.S.C. 154(b) by 0 days.

(21) Appl. No.: 13/748,912

(22) Filed: Jan. 24, 2013

(65) Prior Publication Data
US 2013/0189169 A1 Jul. 25, 2013

Related U.S. Application Data

(60) Provisional application No. 61/590,006, filed on Jan. 24, 2012.

(51) Int. Cl.
*G01N 31/00* (2006.01)
(52) U.S. Cl.
USPC .................................. 436/18; 562/559
(58) Field of Classification Search
USPC .................................. 436/18; 562/559
See application file for complete search history.

(56) References Cited

U.S. PATENT DOCUMENTS

| | | | |
|---|---|---|---|
| 4,172,072 A | * | 10/1979 | Ashmead ............... 530/345 |
| 2005/0272095 A1 | | 12/2005 | Wang |
| 2006/0058390 A1 | * | 3/2006 | Sunkara ............... 514/562 |

OTHER PUBLICATIONS

Ren et al., Growth and physiological responses to supplemental UV-B radiation of two contrasting poplar species, Tree Physiology 26, 665-672 (2006).*
Barnes, Stephen, et al., "High-resolution mass spectrometry analysis of protein oxidations and resultant loss of function," Biochem. Soc. Trans., Oct. 2008, pp. 1037-1044, vol. 36, Pt. 5.
Bern, Marshall, et al., "Conversion of Methione to Homocysteic Acid in Heavily Oxideized Proteomics Samples," Rapid Commun. Mass Spectrom., Mar. 2010, pp. 768-772, vol. 24, No. 6.
Rusnak, Felicia, et al., "A Parallel Method for Desalting and Concentrating Microliter Volume Samples for Mass Spectrometry," J. Biomol. Tech., Mar. 2000, pp. 12-19, vol. 11, No. 1.
Zong, Wansong, et al.,"The oxidative products of methionine as site and content biomarkers for peptide oxidation," J. Pept. Sci., Mar. 2010, pp. 148-152, vol. 16, No. 3.
Ren, Jian, et al., "Growth and physiological responses to supplemental UV-B radiation of two contrasting poplar species," Tree Physio., May 2006, pp. 665-672, vol. 26, No. 5.

* cited by examiner

*Primary Examiner* — Monique Cole
(74) *Attorney, Agent, or Firm* — McDonnell Boehnen Hulbert & Berghoff LLP

(57) ABSTRACT

The present invention provides reagents and methods for limiting adsorptive and/or oxidative protein losses in a sample.

16 Claims, 5 Drawing Sheets

BUFFERS FOR STABILIZING BIOLOGICAL SPECIMENS AND THEIR USE

CROSS REFERENCE

This application claims priority to U.S. Provisional Patent Application Ser. No. 61/590,006, filed Jan. 24, 2012, incorporated by reference herein in its entirety.

BACKGROUND

There are many situations, such as immunoprecipitation, in the context of protein research that result in low-concentration (<1 micromolar) solutions of proteins of interest. For example, mass spectrometric immunoassay (MSIA) is a high throughput form of immunoprecipitation that may involve simultaneous handling of up to 96 samples. Until recently, the major analytical modality for MSIA was MALDT/TOF mass spectrometry, in which eluted proteins are stamped onto a MALDI target and immediately dried prior to analysis. For many proteins, electrospray ionization (ESI) mass spectrometry provides advantages over MALDI-MS. Attempts to couple MSIA with ESI/MS have been limited in throughput capability because samples have to be eluted individually and introduced into the ESI mass spectrometer one at a time to avoid adsorptive and/or oxidative protein losses while samples sit in autosampler vials (for minutes to hours) waiting to be injected. Thus, reagents and methods to limit such protein loss in samples of interest are needed.

Blood plasma/serum samples are susceptible to artifactual oxidative damage over time during storage in the freezer (even at temperatures as low as −80° C.). This may be due to chemistries that occur in the solid phase or chemistries that occur upon sample thawing and temporary storage in the liquid state. Importantly, this storage-associated oxidative damage may adversely or artifactually affect the outcome of clinical or other analytical measurements made on proteins and other molecules in the sample—leading to inaccurate results. Thus reagents and methods to limit such artifactual oxidation in stored plasma/serum samples are of interest.

SUMMARY OF THE INVENTION

In a first aspect, the present invention provides buffer solutions comprising a thioether compound. In various embodiments, the buffer solution may further comprise a carrier protein and/or an acid. In any of these embodiments, any solvent suitable for use in a buffer of interest may be used, including water, one or more water-miscible organic solvents, or mixtures thereof. In one embodiment, the one or more organic solvents are selected from the group consisting of methanol, acetonitrile, tetrahydrofuran, isopropanol, n-propanol, ethanol, dioxane, dimethyl sulfoxide, dimethylformamide, and methyl ethyl ketone. In a further embodiment, the thioether compound comprises a methionine (Met) compound. In another embodiment, the methionine compound comprises a Met-Ser (serine) dipeptide. In a further embodiment, the buffer solution of comprises a water/organic solvent mixture is in a ratio of 70/30 (v/v). In another embodiment, the concentration of the thioether compound is between about 0.1 mM and 15 mM, or between about 1 mM and 5 mM.

In another embodiment, the carrier protein is a polyclonal antibody, including but not limited to an anti-human albumin IgG antibody. Any suitable concentration of carrier protein can be used, such as between about 50 nM and 500 nM or between about 100 nM and 200 nM. In a further embodiment, the acid may comprise trifluoroacetic acid, which can be present at any suitable concentration, such as between about 0.1% and 5.0% v/v or between about 0.4% and 0.6% v/v.

In a second aspect, the present invention provides compositions, comprising
 (a) a thioether compound; and
 (b) one or more components selected from the group consisting of
  (i) heparin;
  (ii) sodium citrate;
  (iii) citrate, phosphate, and dextrose
  (iv) citrate, theophylline, adenosine, and dipyridamole (CTAD);
  (v) EDTA;
  (vi) potassium oxalate and sodium fluoride
  (vii) sodium fluoride and EDTA
  (viii) sodium fluoride; and
  (ix) a bacteriostatic component.

The compositions of this aspect of the invention are particularly suited for use in combination with biospecimen collection or storage containers, to decrease biomolecule oxidation in samples of stored biomolecules, such as bodily fluid samples and other tissue samples. In one embodiment, the compositions of the second aspect of the invention comprise powdered compositions. Any embodiment or combination of embodiments of the first aspect of the invention can be used in this second aspect of the invention.

In a third aspect, the present invention provides biomolecule collection or storage containers, wherein the biomolecule collection or storage container comprises a coating on an inner surface of the container, wherein the coating comprises a thioether compound. The thioether compound may comprise any embodiment of thioether compounds disclosed herein, and may further comprise additional components according to any embodiment or combination of embodiments disclosed herein.

In a fourth aspect, the present invention provides methods for reducing protein loss and/or biomolecule oxidation in low-concentration target biomolecule solutions comprising storing the target biomolecule in the buffer solution any embodiment or combination of embodiments of the first aspect of the invention.

In a fifth aspect, the present invention provides methods for reducing protein loss and/or biomolecule oxidation in low-concentration target biomolecule solutions comprising storing the target biomolecule in a container of any embodiment or combination of embodiments of the third aspect of the invention.

DETAILED DESCRIPTION OF THE INVENTION

Figure 1:
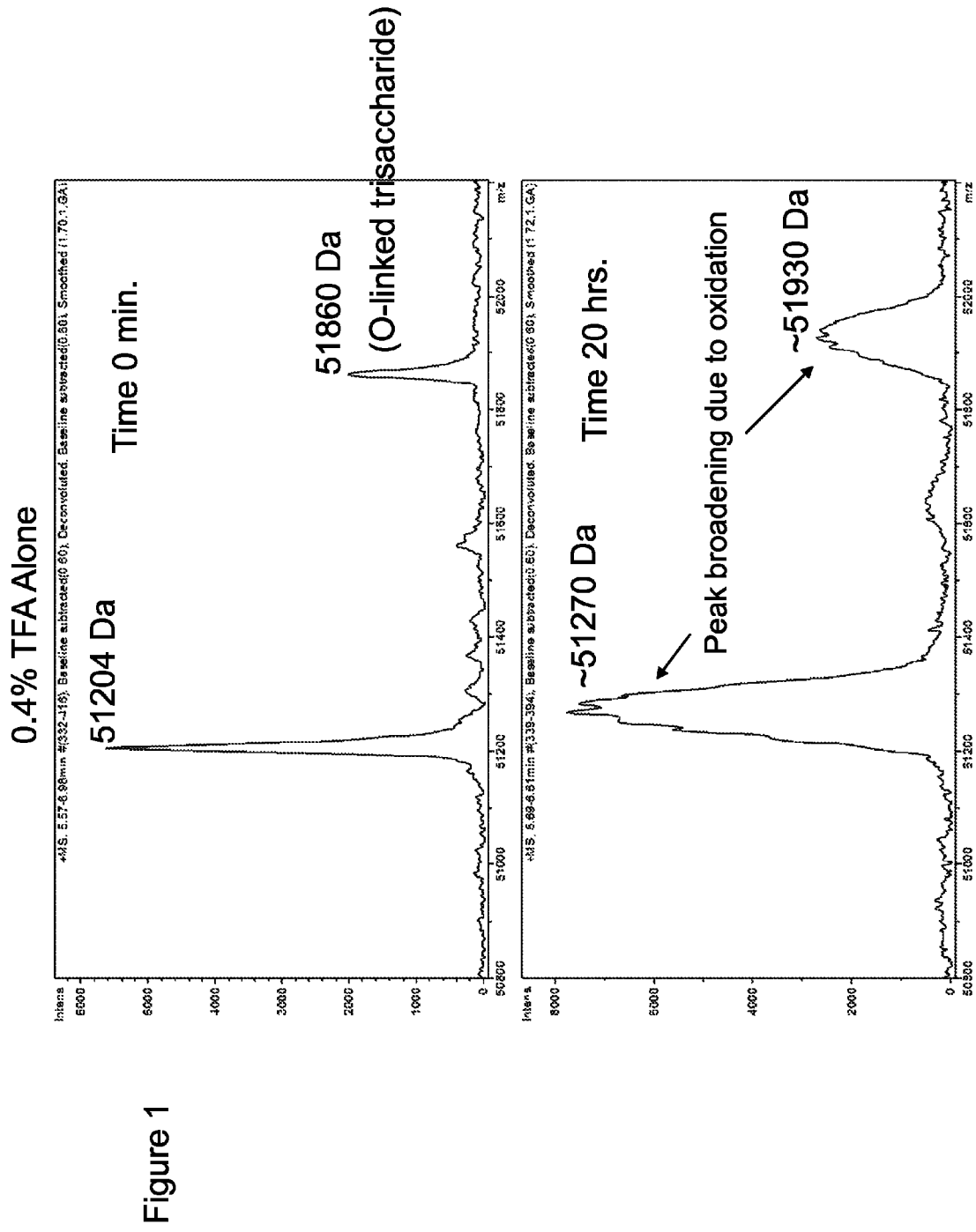
FIG. 1. Charge deconvoluted ESI-mass spectra taken at various time points from control buffer sample containing 0.4% TFA only.

All embodiments disclosed herein can be combined with any other embodiment unless the context clearly indicates otherwise. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number, respectively. Additionally, the words "herein," "above," and "below" and words of similar import, when used in this application, shall refer to this application as a whole and not to any particular portions of this application. As used herein, the singular forms "a", "an" and "the" include plural referents unless the context clearly dictates otherwise. "And" as used herein is interchangeably used with "or" unless expressly stated otherwise.

As used herein "about" means +/−5% from the cited parameter.

In a first aspect, the present invention provides buffer solutions comprising a thioether compound, optionally a carrier protein, and optionally an acid. The buffer solutions may be used, for example, to reduce protein loss and/or limit biomolecule oxidation in biomolecule-containing solutions. The buffer solutions as disclosed herein are useful, for example, in biospecimen/biomolecule stabilization (as discussed below), certain laboratory assays and analytical methods, including immunoprecipitation and high-throughput immunoprecipitation such as mass spectrometric immunoassay (MSIA). In particular, the invention is useful where MSIA is coupled with electrospray ionization (ESI) mass spectrometry. The buffer solutions of the invention overcome prior problems with such assays and analytical methods by minimizing protein loss (including adsorptive loss and loss due to oxidation) of low-concentration solutions of a target protein to be analyzed, allowing for longer-term storage and use of such sample solutions. Significantly, the buffer solutions of the invention do not interfere with the analysis of target proteins in solution by liquid chromatography-mass spectrometry (LC-MS), and allow the protein solutions to sit in, e.g., test tubes or autosampler vials for hours or, in some instances, days, prior to analysis.

As used herein, the term "buffer solution" refers to any liquid solution containing one or more solubilized reagents. In some embodiments the buffer solution is an aqueous solution. In other embodiments the buffer solution comprises one or more water-miscible organic solvents. In other embodiments, the solvent of the buffer solution is a mixture of water and one or more water-miscible organic solvents. Water-miscible organic solvents that may be used with the invention include, but are not limited to, methanol, acetonitrile, tetrahydrofuran, isopropanol, n-propanol, ethanol, dioxane, dimethyl sulfoxide, dimethylformamide, and methyl ethyl ketone, or a combination thereof.

One of skill in the art will appreciate that in the embodiments where the buffer solution comprises a mixture of water and one or more water-miscible organic solvents, the ratio of water to organic solvent, as well as the particular organic solvent(s) to be used, may vary depending on factors such as the particular target protein to be analyzed, the particular analytical techniques to be utilized, and the anticipated storage time of the sample solutions to be analyzed. In certain embodiments, the water/organic solvent ratio is about 70/30 (v/v), in others it is about 60/40 (v/v), 50/50 (v/v), 40/60 (v/v), 90/10 (v/v), or about 80/20 (v/v). Buffer solutions comprising primarily one or more organic solvents in combination with water, e.g. an about 10/90 (v/v) solution, are also contemplated. It will be understood by one of skill in the art that the percentage of organic solvent to be used will depend on the particular organic solvent(s) used as well as the nature of the target protein. In particular, one of skill in the art will understand that the percentage of organic solvent(s) used should be restricted to where non-covalent adducts with the target protein do not form, or, depending upon the exact application, are at least minimized, in order to avoid interference with other, protein-related peaks of interest and difficulties in data interpretation.

As used herein, the term "thioether compound" refers to any chemical entity containing a thioether moiety. Preferably, the thioether compound is non-volatile. In certain embodiments, the thioether moiety is, for example, diethyl sulfide or bis(methylthio)methane. In other embodiments, the thioether compound is a methionine compound, which, as used herein, refers to any chemical entity containing the amino acid methionine. Methionine compounds include methionine with any or no protecting groups on the amino- or carboxy-groups. Methionine compounds also include those compounds in which the methoinone moiety is modified, such as methionine without the amino group or without the carboxyl group. Methionine compounds also include peptides containing methionine, optionally protected at the N- and/or C-termini. In certain embodiments, the methionine compound is a Met-Ser dipeptide. One of skill in the art will understand that the thioether compound selected should be one that does not produce non-covalent adducts with the target protein, and that it may be possible to convert a particular thioether compound, e.g. a methione compound, from a compound that forms non-covalent adducts to one that does not, and is therefore suitable for use in the buffers of the invention, by way of modification of the thioether compound.

Without intending to be bound by any theory, it is believed that it is the thioether functional group of the methionine compound that prevents oxidation of the target protein from ambient oxygen due to exposure to air. In certain embodiments, the concentration of the thioether compound is between about 0.1 mM and about 500 mM. In other embodiments, the concentration is between about 0.1 mM and about 250 mM, about 0.1 mM and about 100 mM, about 0.1 mM and about 50 mM, about 0.1 mM and about 15, mM, about 0.1 mM and about 5 mM, about 0.1 mM and about 500 mM, about 1 mM and about 250 mM, about 1 mM and about 100 mM, about 1 mM and about 50 mM, about 1 mM and about 15, and about 1 mM and about 5 mM. As used herein when referring to numerical ranges, the term "between" includes the outer ranges recited, e.g. between about 1 mM and about 5 mM means between about 1 mM and about 5 mM, inclusive of about 1 mM and about 5 mM. Additionally, as used herein when referring to numerical ranges, the reference is intended to include within its scope any value or range falling within the recited range, even if not explicitly stated, e.g. between about 1 mM and about 5 mM encompasses, e.g. between about 2 nM and about 3.5 nM and also encompasses, e.g. about 3.5 nM. Preferably, the concentration of the thioether compound is below the level at which detectable non-covalent adducts are formed with the target protein to be analyzed. It will be understood by one of skill in the art that the concentration of the thioether compound to be used will depend on the particular environment to which the target protein is exposed, i.e. a higher concentration of thioether compound will be required where the target protein is exposed to a highly oxidizing environment.

As used herein, the term "carrier protein" means any protein capable of reducing adsorptive loss of a target protein when contained within a buffer solution with the target protein. Adsorptive loss refers to the lowering of the concentration of a molecule in solution due to adhesion of the molecule onto the surface of the container holding the solution. Preferably, the carrier protein is one whose peaks would not appear anywhere near those of the target protein in a mass spectrum. In some instances, inclusion of the carrier protein in the buffer solution may be omitted. One of skill in the art will understand that in circumstances, e.g., where the target protein is highly abundant in the solution from which it was extracted, and therefore of a generally higher concentration (e.g., >1 micromolar) in the final solution to be analyzed, the carrier protein may not be need. The need may be assessed empirically.

In certain embodiments, the carrier protein is an antibody. In certain embodiments, the carrier protein is a monoclonal antibody, and in other embodiments the carrier protein is a polyclonal antibody, each preferably in the low hundreds of nanomolar concentration range; such carrier proteins have a high mass/mole ratio and tend to chromatographically elute separately from target proteins without introducing extra peaks into the mass spectra of the target proteins. In other embodiments, the carrier protein is a protein that is heavily glycosylated with a high polydispersity index, for example bovine fetuin; such carrier proteins tend to produce many different peaks in a mass spectrum such that, at the concentration utilized, each molecularly unique version of the protein fails to make a distinct peak, rendering the carrier protein "invisible" in the mass spectrum. In some embodiments, the concentration of the carrier protein is between about 50 nM and about 1 µM, between, about 50 nM and about 500 nM, or between about 100 nM and about 200 nM. One of skill in the art will understand that the concentration of the carrier protein should be kept within a level that avoids interference with the peaks of the target protein, and that avoids the introduction of ill-defined humps in the higher m/z range of the mass spectrum.

In certain embodiments, the buffer solution may contain an acid, which may assist in the analytical method to be utilized by, for example, imparting a net positive charge upon the target protein to facilitate the ionization/desolvation process in a mass spectrometer. Where immunoprecipitation is used, the acid may mediate protein elution during the immunoprecipitation process. One of skill in the art will understand that if the analytical method to be used does not involve, e.g., elution of an affinity captured target protein from an antibody (or other protein), then acid may be unnecessary, but that in certain analytical methods, inclusion of an acid is appropriate. The specific acid to be selected is within the knowledge of one of skill in the art. In certain embodiments, the acid is an organic acid, for example trifluoroacetic acid, trfluoromethanesulfonic acid, benzenesulfonic acid, or methanesulfonic acid. Where the acid is TFA, in certain embodiments the concentration is between about 0.1% and about 5.0% v/v, in other embodiments the concentration is between about 0.1% and about 3.0% v/v, between about 0.1% and about 1.5% v/v, between about 0.1% and about 0.8% v/v, or between about 0.4% and about 0.6% v/v. The concentration of the acid to be used may be ascertained by one of skill in the art.

As used herein, the term "target protein" refers to any protein to be analyzed or assayed by any method in which the protein is to be in solution, including, but not limited to, mass spectrometry, mass spectrometric immunoassay, and electrospray ionization mass spectrometry. As used herein "low-concentration target protein solution" means a solution of a target protein having a concentration less than about 1 micromolar.

As used herein, the term "protein loss" refers to any effective loss of protein concentration in a solution. Protein loss may include loss from solution due to adsorption, or loss due to protein degradation, oxidation, or other chemical modifications.

In a second aspect, the present invention provides compositions, comprising
(a) a thioether compound; and
(b) one or more components selected from the group consisting of
 (i) heparin;
 (ii) sodium citrate;
 (iii) citrate, phosphate, and dextrose;
 (iv) citrate, theophylline, adenosine, and dipyridamole (CTAD);
 (v) EDTA;
 (vi) potassium oxalate and sodium fluoride
 (vii) sodium fluoride and EDTA
 (viii) sodium fluoride; and
 (ix) a bacteriostatic component.

The compositions of this aspect of the invention are particularly suited for use in combination with biomolecule collection containers, to limit protein loss and decrease biomolecule oxidation in samples of stored biomolecules, such as bodily fluid samples and other tissue samples. In one embodiment, the compositions of the second aspect of the invention comprise powdered compositions. Any embodiment or combination of embodiments of the first aspect of the invention can be used in this second aspect of the invention, unless the context clearly dictates otherwise. For example, in certain embodiments, the concentration of the thioether compound is between about 0.1 mM and about 500 mM. In other embodiments, the concentration is between about 0.1 mM and about 500 mM. In other embodiments, the concentration is between about 0.1 mM and about 250 mM, about 0.1 mM and about 100 mM, about 0.1 mM and about 50 mM, about 0.1 mM and about 15, mM, about 0.1 mM and about 5 mM, about 0.1 mM and about 500 mM, about 1 mM and about 250 mM, about 1 mM and about 100 mM, about 1 mM and about 50 mM, about 1 mM and about 15, and about 1 mM and about 5 mM. In a further embodiment, the thioether compound is present such that a final in-solution concentration of between about 1 mM to about 1,000 mM. In other words, if a powdered form is used, the amount provided in the composition is one that would result in a concentration of between about 1 mM to about 1,000 mM upon reconstitution, such as when mixed with a biomolecule-containing solution as discussed in the methods of the invention. In various further embodiments, the thioether compound is present such that a final in-solution concentration of between about 1 mM to about 500 mM; about 1 mM to about 250 mM; and about 1 mM to about 100 mM.

By way of further non-limiting example, the thioether moiety is, for example, diethyl sulfide or bis(methylthio)methane. In other embodiments, the thioether compound is a methionine compound, which, as used herein, refers to any chemical entity containing the amino acid methionine. Methionine compounds include methionine with any or no protecting groups on the amino- or carboxy-groups. Methionine compounds also include those compounds in which the methionine moiety is modified, such as methionine without the amino group or without the carboxyl group. Methionine compounds also include peptides containing methionine, optionally protected at the N- and/or C-termini. In certain embodiments, the methionine compound is a Met-Ser dipeptide.

The methionine compounds for use in the compositions of the invention can also be further combined with any of the other components or combinations thereof disclosed in the first aspect of the invention.

The composition may be in any suitable form, including in solution (preferably with an aqueous solvent), in powdered form, or frozen. The compositions may be prepared as such, or they may be combined at the time of use, for example, at the time of coating biospecimen collection/storage devices, such as tubes for biobanking serum or plasma.

The one or more additional components are components used in blood or urine collection/storage; thus, their combination with the thieother compounds is particularly suited for use with blood and urine collection and storage containers, such as tubes for biobanking serum or plasma. Any suitable amount of the one or more components for an intended use may be present in the compositions of the invention; determining such appropriate amounts of the one or more additional components is well understood by those of skill in the art. In one non-limiting embodiment, any suitable bacteriostatic can be used, including but not limited to a combination of boric acid, sodium formate, and sodium borate, as are used in some commercially available urine collection/storage containers. In another embodiment, the heparin may comprise any suitable form of heparin, including but not limited to ammonium heparin, sodium heparin, and lithium heparin.

In a third aspect, the present invention provides biospecimen collection or storage containers, wherein the biospecimen collection or storage container comprises a coating on an inner surface of the container (or simply addition of the desired material to the container) to be mixed upon addition of the liquid specimen, wherein the coating comprises a thioether compound. The thioether compound may comprise any embodiment of thioether compounds disclosed herein. For example, in certain embodiments, the concentration of the thioether compound is between about 0.1 mM and about 15 mM. In other embodiments, the concentration is between 1 mM and 1,000 mM. By way of further non-limiting example, the thioether moiety is, for example, diethyl sulfide or bis(methylthio)methane. In other embodiments, the thioether compound is a methionine compound, which, as used herein, refers to any chemical entity containing the amino acid methionine. Methionine compounds include methionine with any or no protecting groups on the amino- or carboxy-groups. Methionine compounds also include those compounds in which the methionine moiety is modified, such as methionine without the amino group or without the carboxyl group. Methionine compounds also include peptides containing methionine, optionally protected at the N- and/or C-termini. In certain embodiments, the methionine compound is a Met-Ser dipeptide. The methionine compounds for use in the compositions of the invention can also be further combined with any of the other components or combinations thereof disclosed in the first aspect of the invention In a further embodiment, the coating or added material may comprise a composition according to any embodiment or combination of embodiments of the second aspect of the invention. Thus, the coating may comprise:
(a) a thioether compound; and
(b) one or more components selected from the group consisting of
(i) heparin;
(ii) sodium citrate;
(iii) citrate, phosphate, and dextrose
(iv) citrate, theophylline, adenosine, and dipyridamole (CTAD);
(v) EDTA;
(vi) potassium oxalate and sodium fluoride
(vii) sodium fluoride and EDTA
(viii) sodium fluoride; and
(ix) a bacteriostatic component.

As used herein, a "coating" refers to any application of the thioether and any additional components to an internal wall of the container. In one embodiment, the coating comprises a powder of the thioether and any additional components on an internal wall of the container. Alternatively, the thioether and any additional components may be present as a liquid or powder that is present in the container, for example, at the bottom wall, and which is mixed with a collected sample laced into the container by an attending technician, such as a technician collecting a blood sample.

The containers may be any suitable container, including but not limited to tubes (glass, plastic, etc.), cups, bags, vials, etc. In one embodiment, the containers are blood collection tubes or tubes for bio-banking serum or plasma.

In a fourth aspect, the present invention provides methods for reducing protein loss and/or biomolecule oxidation in target biomolecule solutions comprising storing the target biomolecule in the buffer solution or composition according to any embodiment or combination of embodiments of the first or second aspect of the invention.

In a fifth aspect, the present invention provides methods for reducing protein loss and/or biomolecule oxidation in low-concentration target biomolecule solutions comprising storing the target biomolecule in a container of any embodiment or combination of embodiments of the third aspect of the invention.

In these methods of the fourth and fifth aspects of the invention, any embodiment or combination of embodiments of the first, second, or third aspects of the invention can be used unless the context clearly dictates otherwise. For example, in certain embodiments, the concentration of the thioether compound is between about 0.1 mM and about 500 mM. In other embodiments, the concentration is between about 0.1 mM and about 250 mM, about 0.1 mM and about 100 mM, about 0.1 mM and about 50 mM, about 0.1 mM and about 15, mM, about 0.1 mM and about 5 mM, about 0.1 mM and about 500 mM, about 1 mM and about 250 mM, about 1 mM and about 100 mM, about 1 mM and about 50 mM, about 1 mM and about 15, and about 1 mM and about 5 mM. In a further embodiment, the thioether compound is present such that a final in-solution concentration of 1 to 1,000 mM. In other words, if a powdered form is used, the amount provided in the composition is one that would result in a concentration of 1 to 1,000 mM upon reconstitution, such as when mixed with a biomolecule-containing solution as discussed in the methods of the invention.

By way of further non-limiting example, the thioether moiety is, for example, diethyl sulfide or bis(methylthio)methane. In other embodiments, the thioether compound is a methionine compound, which, as used herein, refers to any chemical entity containing the amino acid methionine. Methionine compounds include methionine with any or no protecting groups on the amino- or carboxy-groups. Methionine compounds also include those compounds in which the methionine moiety is modified, such as methionine without the amino group or without the carboxyl group. Methionine compounds also include peptides containing methionine, optionally protected at the N- and/or C-termini. In certain embodiments, the methionine compound is a Met-Ser dipeptide.

The "target biomolecule" may be any suitable target biomolecule, such as a protein. The biomolecule solution may be any suitable solution, including but not limited to any type of blood sample (or component(s) thereof including serum and plasma), urine, semen, cerebrospinal fluid, synovial fluid, sputum, saliva, tears, ascites fluid, bile or other internal juices, secretions or fluids, and laboratory samples such as samples generated during immunoprecipitation and high-throughput immunoprecipitation such as mass spectrometric immunoassay (MSIA).

In one embodiment, blood plasma/serum samples are susceptible to artifactual oxidative damage over time during storage in the freezer (even at temperatures as low as −80° C.). This may be due to chemistries that occur in the solid phase or chemistries that occur upon sample thawing and temporary storage in the liquid state. Importantly, this storage-associated oxidative damage may adversely or artifactually affect the outcome of clinical or other analytical measurements made on proteins and other molecules in the sample—leading to inaccurate results.

EXAMPLES

Example 1

The following buffer solutions were prepared:

Buffer Solution A: An aqueous solution containing 0.4% (v/v) trifluoroacetic acid, 100 nanomolar (nM) polyclonal anti-albumin antibody, and 1 mM Methionine-Serine (Met-Ser) dipeptide was prepared.

Buffer Solution B: A solution of 70/30 (v/v) water/dimethylsufoxide (DMSO) containing 0.6% trifluoroacetic acid, 100 nM polyclonal albumin antibody, and 1 mM Met-Ser was prepared.

Example 2

Human vitamin D binding protein was extracted from human plasma by MSIA and eluted using various buffer solutions as described below. Deconvoluted ESI-mass spectra were taken at various time points, the times being the elapsed time between elution from the MSIA tip and injection onto the liquid chromatograph-mass spectrometer. The plasma sample used in FIG. 1 possesses a different genotype and accompanying phenotype than the plasma sample used in FIGS. 2 and 3.

Sample 1: An aqueous buffer solution containing 0.4% TFA only was used, and spectra taken at 0 minutes and 20 hours. Peak broadening was observed at 20 hours due to protein oxidation, as shown in FIG. 1.

Figure 2:
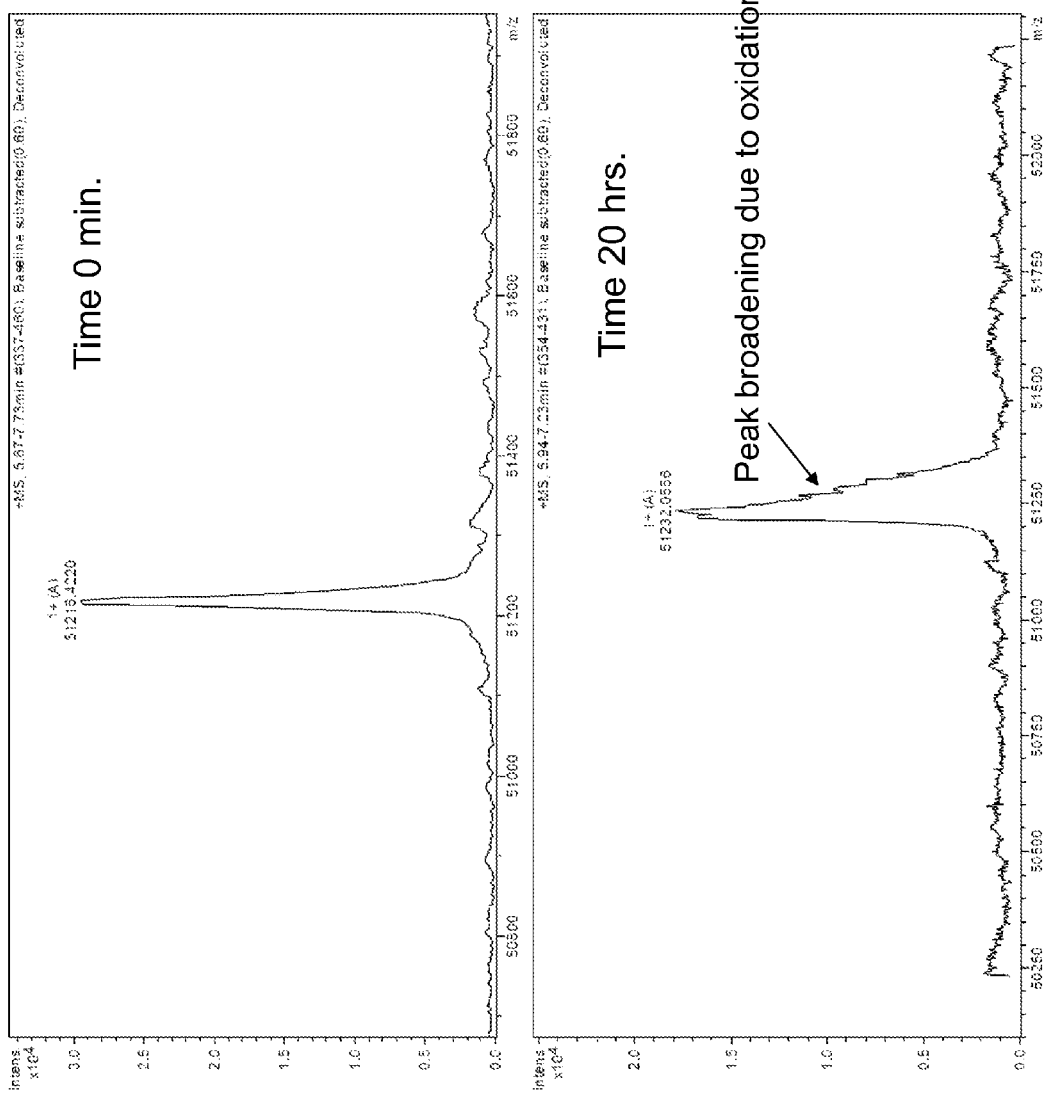
FIG. 2. Charge deconvoluted ESI-mass spectra taken at various time points from control buffer sample containing 0.4% TFA with 100 nM antibody as a carrier.

Sample 2: An aqueous buffer solution containing 0.4% TFA with 100 nM antibody as a carrier protein was used, and spectra taken at 0 minutes and 20 hours. Peak broadening was observed at 20 hours due to protein oxidation, as shown in FIG. 2.

Figure 3:
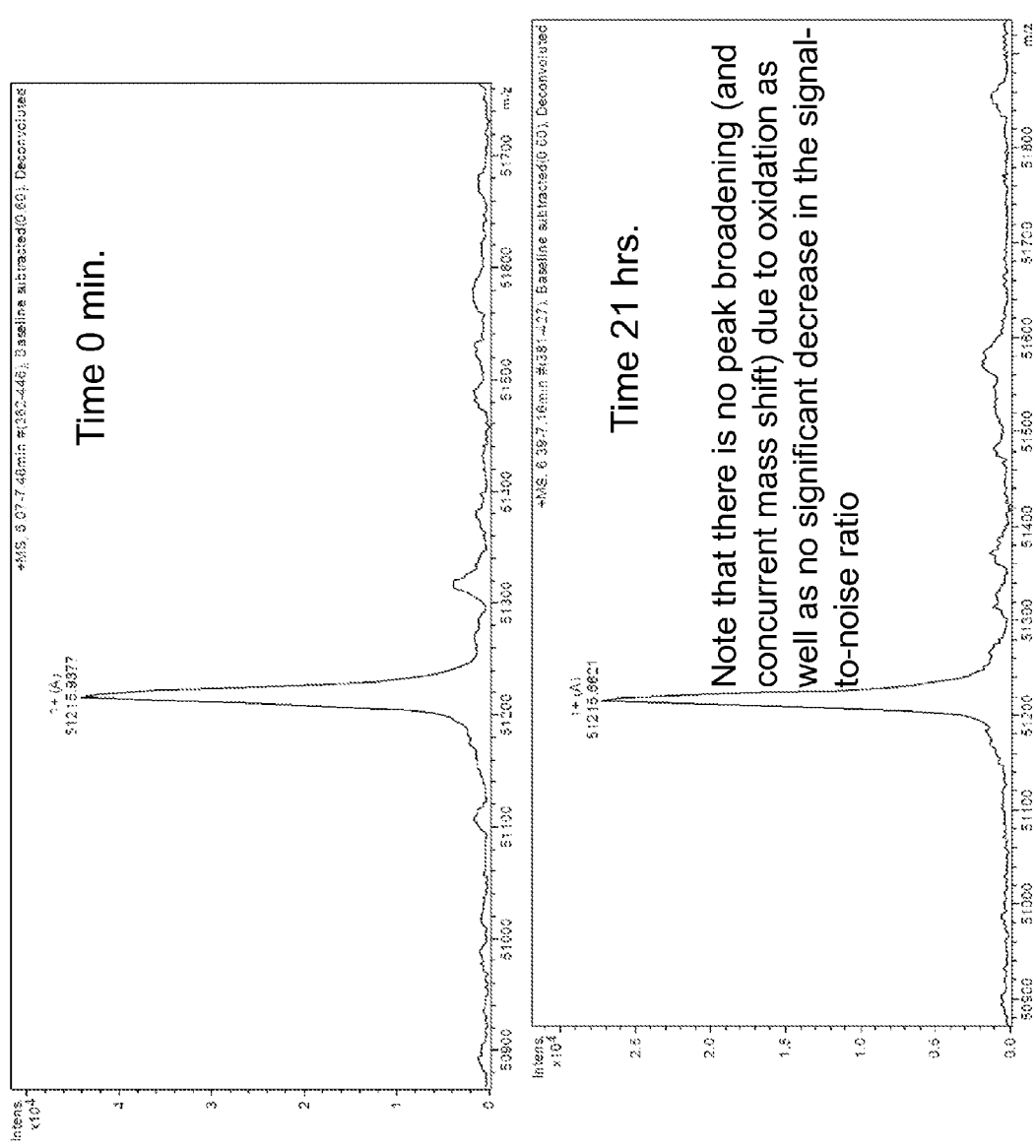
FIG. 3. Charge deconvoluted ESI-mass spectra taken at various time points from control buffer sample containing 0.4% TFA with 100 nM antibody as a carrier and 1 mM FIG. 4. Graph showing percent apolipoprotein A-I (apoAI) methionine oxidation vs. sample age at analysis.

Sample 3: An aqueous buffer solution containing 0.4% TFA with 100 nM antibody as a carrier protein and 1 mM Met-Ser dipeptide as the thioether compound was used, and spectra taken at 0 minutes and 21 hours. No peak broadening or concurrent mass shift was observed, and there was no significant decrease in the signal-to-noise ratio, as shown in FIG. 3.

Example 3

Correlation of Plasma Sample Age with Apolipoprotein A-I (apoAI) Oxidation

Direct correlation between apoA1 methionine residue oxidation and blood plasma sample age strongly suggests ex vivo artifactual oxidation. As an aqueous protein solution, blood plasma/serum proteins are susceptible to artifactual oxidation through the same chemical mechanisms governing the proteins in Example 2 (see Example 4). Thus artifactual oxidation resulting from mistreatment of plasma/serum samples by cumulative time spent in the liquid state (i.e., thawed) will likely be preventable by the same buffers applied in Example 2. Notably, preventable artifactual oxidation may also occur in solid-phase plasma/serum samples stored at −80° C. through a process analogous to everyday "freezer burn".

Figure 4:
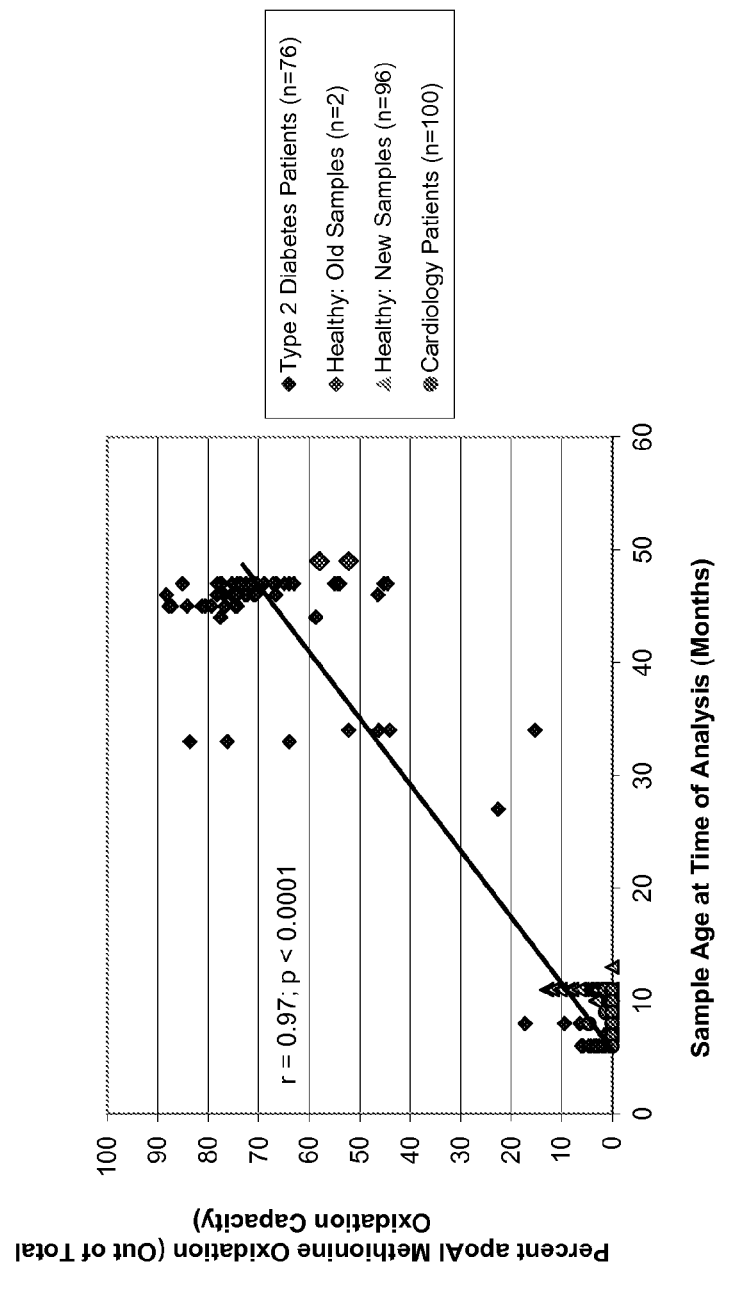

The samples represented in this Example were analyzed by dilute-and-shoot LC-ESI-MS or ESI-based mass spectrometric immunoassay (i.e., MSIA—or pre-isolation prior to analysis by LC-ESI-MS). Analytical methodology did not affect results. All samples were stored at −80° C. prior to analysis, but in different types of vials. The results are shown in FIG. 4.

"Total oxidation capacity" refers to the fact that each molecule of apoA1 protein has 3 methionine residues—meaning that oxidation of all three residues in all protein molecules constitutes complete oxidation and a value of 100 in this plot; analogously, if all apoA1 molecules carried a single oxidized methionine residue the "percent methionine oxidation" would be 33.

"Cardiology Patients" presented to the hospital with angina or heart attack. Type 2 Diabetes Patients and Cardiology Patients are members of the population who, medically, would be expected have the greatest degree of apoAI oxidation. The pearson correlation coefficient (r) applies to all samples considered together.

Example 4

Artifactual Oxidation of apoAI in Blood Plasma

Figure 5:
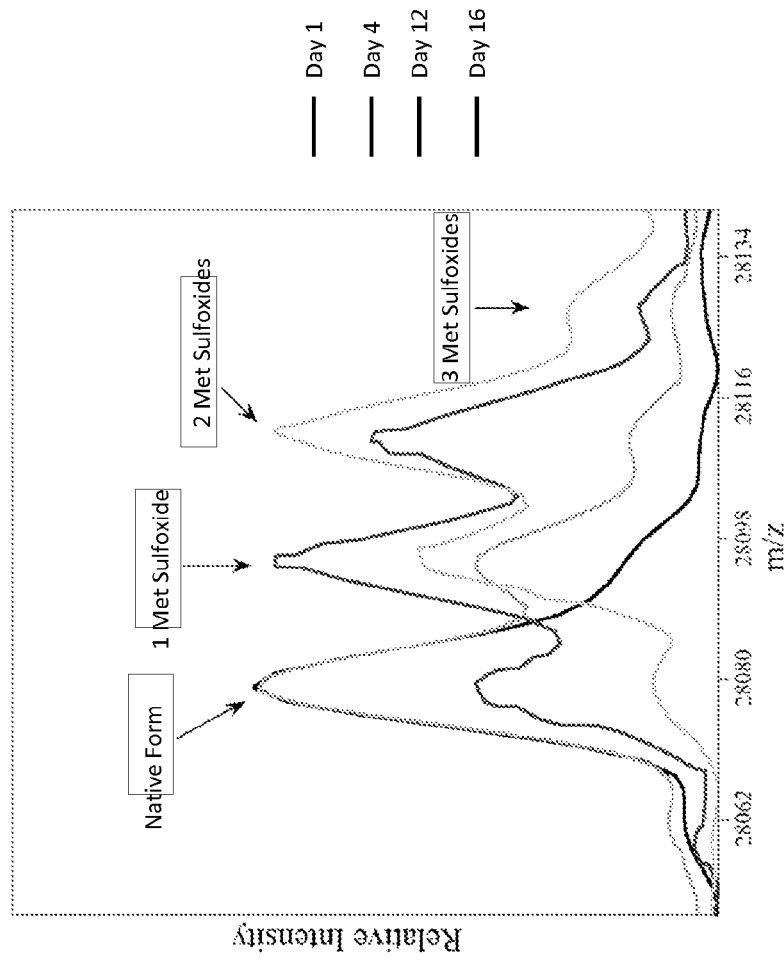
FIG. 5. Charge deconvoluted ESI-mass spectra of apoAI extracted from blood plasma that was left out at room temperature with exposure to air. The progressive artifactual oxidation of apoAI within blood plasma over time is illustrated.

As noted above, since it comprises an aqueous protein solution, blood plasma/serum proteins are susceptible to artifactual oxidation through the same chemical mechanisms governing the proteins in Example 2. Thus, artifactual oxidation resulting from mistreatment of plasma/serum samples by, for example, cumulative time spent in the liquid state (i.e., thawed) will likely be preventable by the same buffers applied in Example 2. This is demonstrated in FIG. 5, which shows charge deconvoluted mass spectra of apoA1 extracted from blood plasma that was left out at room temperature with exposure to air. The data clearly show progressive artifactual oxidation of apoAI within blood plasma over time.

We claim:

1. A buffer solution comprising a thioether compound and a solvent, wherein the buffer solution is characterized by at least one of the following:
    (a) the buffer solution comprises a carrier protein selected from the group consisting of a polyclonal antibody and anti-human albumin IgG antibody, wherein the carrier protein is present in a concentration of between about 50 nM and about 500 nM; and/or
    (b) the buffer solution comprises an acid, wherein the acid is trifluoroacetic acid (TFA), and wherein the TFA is present in a concentration of between about 0.1% and about 5.0% v/v.

2. The buffer solution of claim 1, wherein the solvent comprises water, one or more water-miscible organic solvents, or a mixture thereof.

3. The buffer solution of claim 2, wherein the solvent comprises one or more organic solvents selected from the group consisting of methanol, acetonitrile, tetrahydrofuran, isopropanol, n-propanol, ethanol, dioxane, dimethyl sulfoxide, dimethylformamide, and methyl ethyl ketone.

4. The buffer solution of claim 2 which solvent comprises a mixture of water and one or more water-miscible organic solvents in a ratio of about 70/30 (v/v).

5. The buffer solution of claim 1, wherein the thioether compound is a methionine compound.

6. The buffer solution of claim 5 wherein the methionine compound is a Met-Ser dipeptide.

7. The buffer solution of claim 1, wherein the concentration of the thioether compound is between about 0.1 mM and about 15 mM.

8. The buffer solution of claim 1, wherein the buffer solution comprises a carrier protein selected from the group consisting of a polyclonal antibody and anti-human albumin IgG antibody, wherein the carrier protein is present in a concentration of between about 50 nM and about 500 nM.

9. The buffer solution of claim 1 wherein the buffer solution comprises an acid, wherein the acid is trifluoroacetic acid (TFA), and wherein the TFA is present in a concentration of between about 0.1% and about 5.0% v/v.

10. The buffer solution of claim 8, wherein the buffer solution comprises an acid, wherein the acid is trifluoroacetic acid (TFA), and wherein the TFA is present in a concentration of between about 0.1% and about 5.0% v/v.

11. The buffer solution of claim 10, wherein the solvent comprises water, one or more water-miscible organic solvents, or a mixture thereof.

12. The buffer solution of claim 11, wherein the solvent comprises one or more organic solvents selected from the group consisting of methanol, acetonitrile, tetrahydrofuran, isopropanol, n-propanol, ethanol, dioxane, dimethyl sulfoxide, dimethylformamide, and methyl ethyl ketone.

13. The buffer solution of claim 11 which solvent comprises a mixture of water and one or more water-miscible organic solvents in a ratio of about 70/30 (v/v).

14. The buffer solution of claim 10, wherein the thioether compound is a methionine compound.

15. The buffer solution of claim 14 wherein the methionine compound is a Met-Ser dipeptide.

16. The buffer solution of claim 10, wherein the concentration of the thioether compound is between about 0.1 mM and about 15 mM.

* * * * *